(12) United States Patent
Reinholt et al.

(10) Patent No.: US 8,270,668 B2
(45) Date of Patent: Sep. 18, 2012

(54) METHOD AND APPARATUS FOR ANALYZING OBJECTS CONTAINED IN A FLOW OR PRODUCT SAMPLE WHERE BOTH INDIVIDUAL AND COMMON DATA FOR THE OBJECTS ARE CALCULATED AND MONITORED

(75) Inventors: Frode Reinholt, Skien (NO); Terje Jørgensen, Skien (NO)

(73) Assignee: Ana Tec AS, Porsgrunn (NO)

( * ) Notice: Subject to any disclaimer, the term of this patent is extended or adjusted under 35 U.S.C. 154(b) by 976 days.

(21) Appl. No.: 11/806,017

(22) Filed: May 29, 2007

(65) Prior Publication Data

US 2008/0031489 A1   Feb. 7, 2008

(30) Foreign Application Priority Data

Jun. 1, 2006   (NO) .................................. 20062520

(51) Int. Cl.
*G06K 9/00* (2006.01)
(52) U.S. Cl. ...................................................... 382/103
(58) Field of Classification Search .................. 382/103, 382/107, 141, 143, 152, 154; 348/154, 155, 348/208.2; 209/594, 596; 73/54.15
See application file for complete search history.

(56) References Cited

U.S. PATENT DOCUMENTS

| | | | | |
|---|---|---|---|---|
| 5,111,410 A * | 5/1992 | Nakayama et al. | ........... | 434/258 |
| 5,501,463 A * | 3/1996 | Gobush et al. | ............... | 473/199 |
| 5,864,395 A * | 1/1999 | Laurberg | ................... | 356/239.6 |
| 5,901,854 A * | 5/1999 | Ishii | ............................... | 209/538 |
| 5,960,098 A * | 9/1999 | Tao | ................................ | 382/110 |
| 6,393,141 B1 * | 5/2002 | Cronshaw et al. | ........... | 382/141 |
| 6,570,608 B1 * | 5/2003 | Tserng | .......................... | 348/143 |
| 6,805,245 B2 * | 10/2004 | Kenneway | .................... | 209/538 |
| 6,999,600 B2 * | 2/2006 | Venetianer et al. | .......... | 382/103 |
| 7,133,537 B1 * | 11/2006 | Reid | .............................. | 382/103 |
| 7,446,869 B2 * | 11/2008 | Canty et al. | .................... | 356/335 |
| 2002/0084172 A1 * | 7/2002 | Toms | ............................ | 198/445 |
| 2003/0156736 A1 * | 8/2003 | Chiu et al. | .................... | 382/103 |
| 2003/0210397 A1 * | 11/2003 | Yagita | .......................... | 356/427 |
| 2004/0151360 A1 * | 8/2004 | Pirard et al. | .................. | 382/141 |
| 2007/0076977 A1 * | 4/2007 | Chen et al. | .................... | 382/276 |

* cited by examiner

*Primary Examiner* — Jason M Repko
*Assistant Examiner* — Shervin Nakhjavan
(74) *Attorney, Agent, or Firm* — Wenderoth, Lind & Ponack, LLP

(57) ABSTRACT

A method and an apparatus for analyzing at least one object. The apparatus includes at least one device for capturing images of the at least one object and a device for generating a relative mutual movement between the at least one image capturing device and the at least one object. The apparatus also includes a device for processing and analyzing images captured by the image capturing device. The relative mutual movement involves a mutual rotational movement between the at least one object and the image capturing device, thus establishing two or more images of the object(s) at various angular positions relative to the image capturing device for further processing and analysis in a computer based image analyzer.

14 Claims, 2 Drawing Sheets

METHOD AND APPARATUS FOR ANALYZING OBJECTS CONTAINED IN A FLOW OR PRODUCT SAMPLE WHERE BOTH INDIVIDUAL AND COMMON DATA FOR THE OBJECTS ARE CALCULATED AND MONITORED

BACKGROUND OF THE INVENTION

1. Technical Field

The present invention relates to a method and an apparatus for analyzing objects. More particularly, the invention relates to analyzing objects contained in a flow or product sample, where data as individual object size and shape, and common data as size distribution, among others can be calculated and monitored.

One embodiment of arranging the flow of objects, that could be objects in a stream, is to form a substantially monolayer or curtain, where the objects are captured by an image processing unit.

2. Description of the Related Art

From EP 0348469 B1 there is known a method of automatic particle analysis and means for performing the same, where size distribution of objects and a deviation of the particles from a desired shape and a desired color can be determined. Samples of the particles are flowing out of a silo and down onto a vibrating plate, thus generating a flowing monolayer object curtain. The particles are allowed to fall over an edge of the plate. The curtain is lighted and pictures thereof are recorded at least one place. The pictures are then analyzed, particularly with respect to particle size distribution in the flow and deviation from desired shape.

One shortcoming related to this type of analyzing technique is that the imaging equipment records the shape and extent of a particle in just two dimensions (2-D), and is therefore best suited for homogeneous objects or spheres. However, when analyzing inhomogeneous objects, the third dimension of the particle (the dimension orthogonal to the imaging plane), will remain somewhat unknown by using this type of prior art equipment.

SUMMARY OF THE INVENTION

With the present invention it is now possible to image and process objects in substantial three dimensions (3-D) by the means of one image recording unit. This is achieved by means of a controlled propagation and rotation of the objects together with an algorithm that collects and calculates the images captured of the individual objects by the image recording unit as it passes through the measuring volume.

These and further advantages can be achieved by the invention as defined in the accompanying claims.

BRIEF DESCRIPTION OF THE DRAWINGS

In the following, the present invention shall be further described by means of examples and figures where.

DETAILED DESCRIPTION OF THE INVENTION

Figure 1:
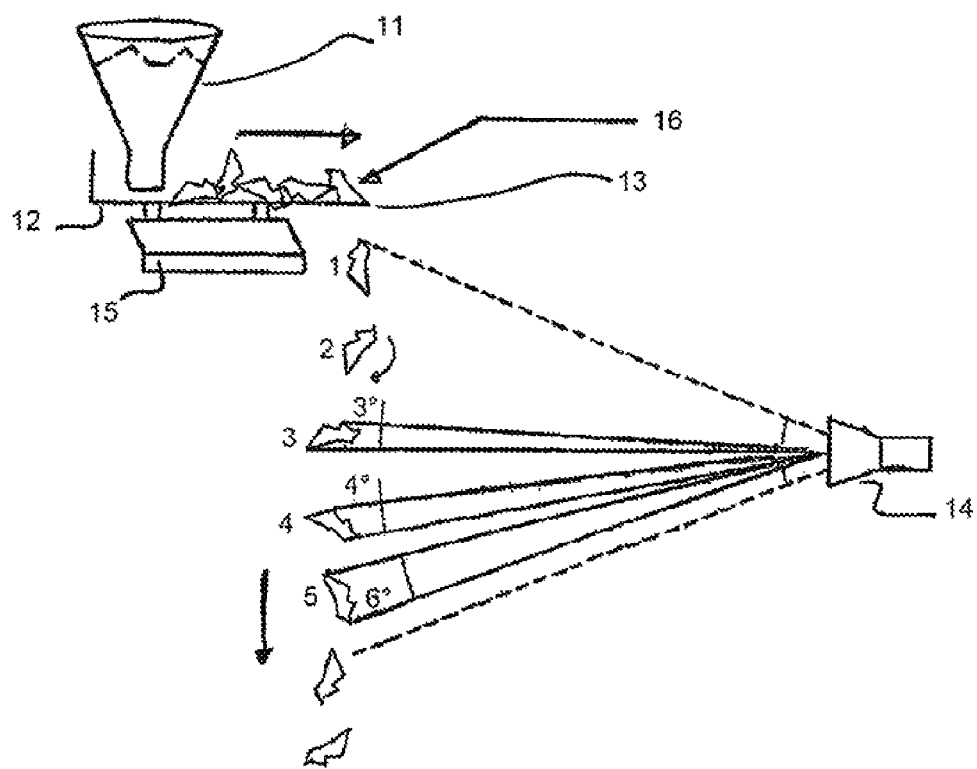
FIG. 1 is a schematic drawing of the 3-D imaging apparatus in accordance with the present invention.
Figure 2:
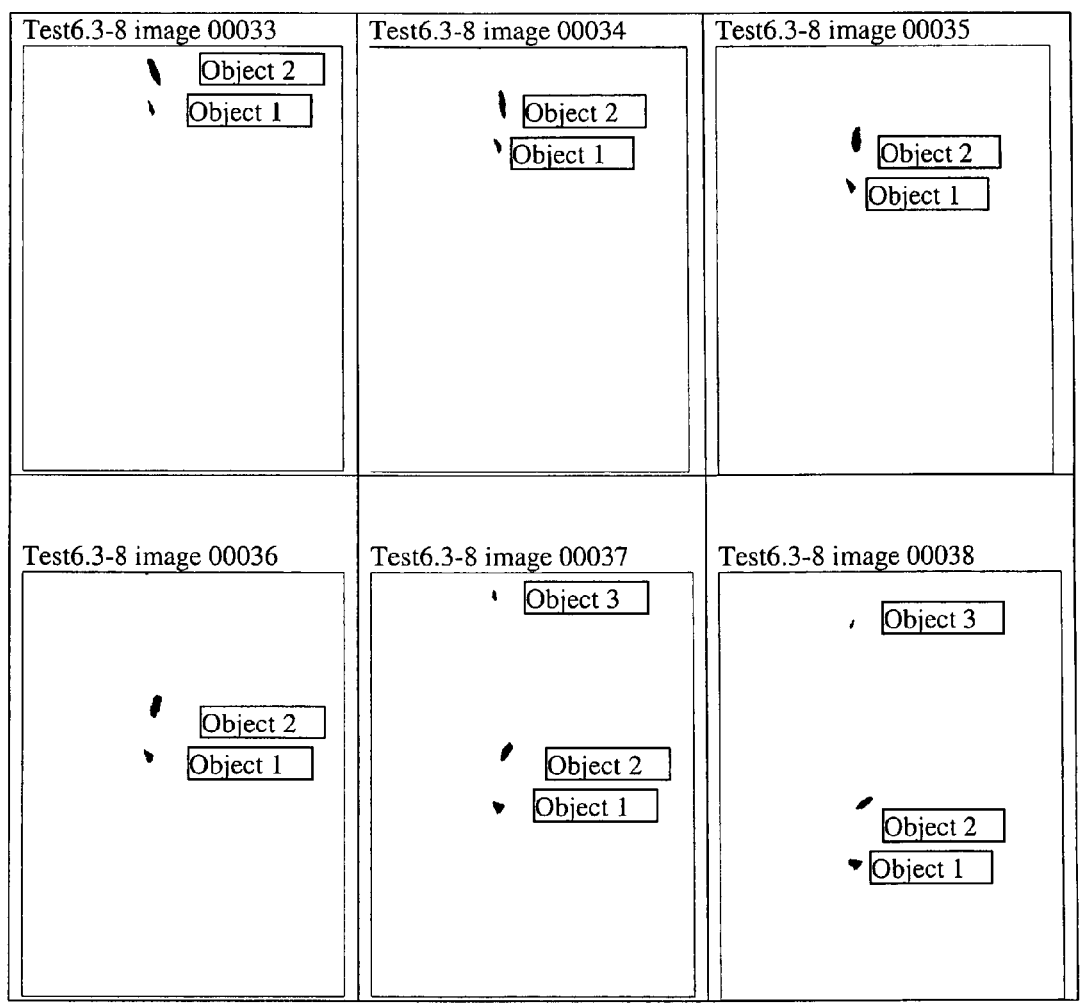
FIG. 2 shows real images of falling objects, captured by the apparatus shown in FIG. 1.

The 3D imaging can be performed by a setup as shown in FIG. 1.

Here the sample is poured into one funnel 11. The sample (objects 16) is then fed by the vibrator plate 12 and falls off the edge 13 of this plate. The rotation is due to the effect of gravity and partial support on the feeder plate and also due to the movement of the vibration feeder 15. The rotation starts as the object slides off the feeder plate.

The objects 16 in the sample then fall and rotate into the measuring volume where the imaging system 14 captures multiple images of objects in the sample. Typically, each individual object is captured many times as shown by the numbers on the left side identifying the instances captured of one of the many objects falling.

There can be a lot of objects of different shape and size in each image.

The object(s) are captured by using a high speed imaging system with a frame rate high enough to give multiple images (2 or more images) of the object(s) as they are passing the measuring volume (or area covered by the camera).

The rotation of the objects can be generated by the way they are fed into the measuring volume.

One method of introducing the objects into the measuring volume is by using a vibrator feeder 15, and when the objects fall down at the end of the feeder, the gravity force creates a rotation since part of the object is supported by the feeder and the other part of the object is influenced by the gravitational field. This will create a rotation.

Other methods of ensuring that a rotation is obtained can be to use some sort of mechanical excitation device that acts on the objects as they leave the feeder. This could be a vibrating "string" positioned at the feeder outlet.

Other methods of feeding the objects and generating rotation could be to use a conveyor belt, pneumatic nozzle, sliding system, feeding by drum, etc.

The object numbered 1, 2, 3, 4 and 5 is the same object in consecutive images, see FIG. 1. This gives different projection areas as indicated in the figure due to rotation of the objects. See also Error! Reference source not found, where real captured images are shown, the same objects are recognized and identified in consecutive images.

Each individual object is recognized in consecutive images by using the law of physics. This can be done by using the characteristics of the force field governing the motion of the object(s) in order to estimate the next position and recognize the same object(s) multiple times in consecutive images.

The objects can also be recognized if they have a known velocity, e.g. on a conveyor belt or in a liquid cell or the similar.

Other ways to do the recognition is to let the imaging system follow the objects either with linear motion or rotational motion In order to estimate the next position and the movement within the image area when the objects fall in a gravitational field, the distance the object has moved from the feeder when it is observed in the measuring volume can be used to estimate the time the object has been falling. In order to do this, the distance from the feeder to the top of the image, the image height and the time between the images is used. By using all this information, it is possible to estimate the position an object will have in the next image, by using the position of the object in the current image. This method is used for each new image and all the objects observed in each individual image, in order to recognize each individual object multiple times as they move through the measuring volume.

Calculation of Next Position:

The distance an object falls within a time t is given by:

$$y = \frac{1}{2}gt^2$$

The distance from the vibrator feeder to the top of the image ($h_t$) is known, also the height of the image (k) and the number of pixels in the image ($p_m$).

(For objects with low density and small diameter, a formula that takes into consideration the drag coefficient of the object should also be used in order to correct the distance/time in order to give a better estimate.)

If an object is observed at a certain pixel position ($p_{x1}$), then the distance ($p_1$) the object has been falling can be calculated:

$$p_1(p_{x1}) = h_t + \frac{h_i p_{x1}}{p_m - 1}$$

The time this object has been falling:

$$t_1 = \sqrt{2 \frac{h_t + \frac{h_i p_{x1}}{p_m - 1}}{g}}$$

What we want, is to estimate the position this object is likely to occur in the next image taken by the camera at the time:

$$t_2 = t_1 + \Delta t$$

Where $\Delta$ is the time between the two images and equal to 1/FPS, where FPS is the number of images taken pr. second.

The most likely position ($p_2$) for the object in the next image as a function of the pixel position ($p_{x1}$) in the current image (at the time $t_2$) can be expressed by:

$$p_2(p_{x1}) = \frac{1}{2}g\left(\frac{1}{fps} + \sqrt{2\frac{h_t + \frac{h_i p_{x1}}{p_m - 1}}{g}}\right)^2$$

and the most likely pixel position ($p_{x2}$) can be calculated on the basis of $p_2$:

$$p_{x2} = \frac{p_2 - h_t}{h_i}(p_m - 1)$$

→ this gives the function that estimates the next position ($p_{x2}$) as a function of the previous position ($p_{x1}$):

$$p_{x2}(p_{x1}) = \frac{(p_m - 1)\left(\frac{1}{2}g\left(\frac{1}{fps} + \sqrt{2\frac{h_t + \frac{h_i p_{x1}}{p_m - 1}}{g}}\right)^2 - h_t\right)}{h_i}$$

Example:
$h_t = 0.04 =$
$h_i = 0.35$
$g = 9.81 =$
$p_m = 1024$
fps = 50

First observation of the object, $p_{x1} = 39$

By applying the function for $p_{x2}$ (39) the next estimate is 105, then by using 105 as $p_{x1}$, $p_{x2}$ (105) gives 182 as the next estimate etc.

$$\begin{pmatrix} 1 & 39 \\ 2 & 105 \\ 3 & 182 \\ 4 & 271 \\ 5 & 371 \\ 6 & 483 \\ 7 & 606 \\ 8 & 741 \\ 9 & 867 \\ 10 & 1044 \end{pmatrix}$$

The table above shows that we are able to observe the particle 9 times with this setup (Image-height, FPS. etc. . . . ) since it falls outside the image area on the 10th estimate (1044>1024).

Algorithm for Analyzing of Objects in 3D

A camera/frame grabber captures two dimensional images of the flowing/falling monolayer curtain of objects. For each image captured, all the objects in the image are Identified and measured. This is done by scanning the image until an object is found. Then the circumference of the object is traversed and the measurements for this individual object performed. Then the search continues until all objects in the image are identified and measured. This results in a list containing one record for each object in the corresponding image, describing the individual objects in detail.

$$P_{b,n} = \{D_A, L, X_{f-max} \ldots\}$$

Where the index b equals image number and index n is the object number. A, $D_A$, L . . . is area, Diameter based on area, max length etc. . . .

DEFINITIONS $\Delta$ Time between images, i.e. between $t_1$ and $t_2$
A Object area measured
$D_A$ Diameter based on area
$X_{f-max}$ Ferret diameter
($b_2$) Image number b2
($b_1$) Image number b1, previous image
$X(t_1)$ Center point, position where object is observed at time $t_1$ in image $b_1$
$X(t_2)$ Center point, position of a object that has been moving for $t_2 = \Delta + t_1$ and observed in image $b_2$
L Max length of object Next step is to identify objects observed in image ($b_2$) where the same object was observed in the previous image ($b_1$) and give the two instances of the same object the same object number.

This is done by applying the laws of physics governing the motion of an object in a conservative force field, such as the gravitational field. Thereby estimating the position an object in the previous image ($b_1$) would have in image ($b_2$) after moving in the force field for a time $\Delta$, the time between two consecutive images.

The position estimate for each object in ($b_1$) falling for $\Delta$ seconds, is then compared to the actual position of the objects in ($b_2$). If the center point of this estimate is within a certain uncertainty radius in the image plane, for the actual position in ($b_2$) a match is found.

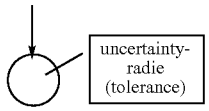

If a match is found for the object in ($b_2$), then the object is accepted as being another representation of the object in ($b_1$) if the area of the object is within a certain size tolerance. Then the object in ($b_2$) is assigned the same number as the object in ($b_1$).

If there is more than one matching object (more than one object with the center point within the uncertainty-radius), the one with size closest to the object in ($b_1$) is selected and given the number of the corresponding object in ($b_1$).

If no objects are found that is within the (uncertainty) tolerance, it will be assigned the next available ordinal object number in the sequence, unless the position of the object in ($b_2$) is larger than $$p_{x2}(0) + \frac{D_A}{2}$$

then the object is discarded.

This will be repeated for all objects in the image ($b_2$), until all have been assigned numbers or discarded.

The same process will be repeated recursively for the next images (trying to find the same objects in the previous image), until all the samples have been fed through the analyzer. 10000 images are taken for a typical sample.

And there might be 1000 to 1000000 objects in the sample and 10 to 1000 objects in each image typically.

After all/parts of the sample are analyzed, a list of object information is available for further processing. An example of the results generated is shown in Table 1:

TABLE 1 the representation of the instances of the objects

| ImgNo | PartNo | A | Da | Xf-min | Xf-max | ... |
|---|---|---|---|---|---|---|
| 1 | 1 | 1 | 1.13 | 0.49 | 1.43 | |
| 2 | 1 | 1.1 | 1.18 | 0.32 | 1.31 | |
| 3 | 1 | 1.2 | 1.24 | 0.28 | 1.85 | |
| 4 | 1 | 0.9 | 1.07 | 0.28 | 1.61 | |
| 1 | 2 | 2 | 1.60 | 0.42 | 3.15 | |
| 2 | 2 | 2.1 | 1.64 | 0.44 | 2.80 | |
| 3 | 2 | 3 | 1.95 | 1.78 | 2.33 | |
| 4 | 2 | 1.8 | 1.51 | 0.58 | 2.27 | |
| 2 | 3 | 5 | 2.52 | 0.63 | 2.95 | |
| 3 | 3 | 4 | 2.26 | 0.64 | 2.93 | |
| 4 | 3 | 3.3 | 2.05 | 1.10 | 4.05 | |
| 2 | 4 | 8 | 3.19 | 0.69 | 5.92 | |
| 3 | 4 | 6 | 2.76 | 0.57 | 4.26 | |
| 4 | 4 | 5 | 2.52 | 1.89 | 3.97 | |
| 5 | 4 | 5.5 | 2.65 | 1.09 | 4.97 | |

By processing the information in Table 1, a better estimate for each object can be found than with 2-D imaging and analysis since more measurements are available for each object.

Example: For object no 1, Xf-max can be estimated to 1.85, Xf-min to 0.28, the area could be estimated by taking an average of all the measured areas etc.

The Area Â could also be estimated by using all available information about the object: $\hat{A}=f(A, D_A, X_{f\text{-}min}, X_{f\text{-}max}, \ldots)$ where the function f can be found by using different optimization techniques in order to give better estimates. (Â means estimated area.)

Also compound measures like L/T-ratio (Length/Thickness) can be found, in our example it will be L/T=1.85/0.28=6.66.

Here we have used the 4 individual measurements of the object to find; the maximum length and the minimum width of object number 1. By using these numbers, we get a better estimate of VT-Ratio than using traditional methods where only a single measurement of the object is used.

While prior art methods would give one of the results in the set [2.92, 4.12, 6.54, 5.77, . . . ] depending on which of the 4 measurements of the object are used.

TABLE 2

L/T ratios based on classical methods

| ImgNo | PartNo | A | Da | Xf-min | Xf-max | L/T |
|---|---|---|---|---|---|---|
| 1 | 1 | 1 | 1.13 | 0.49 | 1.43 | 2.92 |
| 2 | 1 | 1.1 | 1.18 | 0.32 | 1.31 | 4.09 |
| 3 | 1 | 1.2 | 1.24 | 0.28 | 1.85 | 6.61 |
| 4 | 1 | 0.9 | 1.07 | 0.28 | 1.61 | 5.75 |
| | | | | | mean | 4.84 |
| | | | | | sdev | 1.65 |

By processing all instances of all the objects in such a way, a single representation for each object can be achieved with a higher degree of accuracy than that of prior art.

The single object representation might look like (Table 3):

TABLE 3

Processed object information

| Part No | A AVG | Da | Xf-min | Xf-max | L/T | ... |
|---|---|---|---|---|---|---|
| 1 | 1.05 | 1.16 | 0.28 | 1.85 | 6.61 | |
| 2 | 2.23 | 1.68 | 0.42 | 3.15 | 7.50 | |
| 3 | 4.10 | 2.28 | 0.63 | 4.05 | 6.43 | |
| 4 | 6.13 | 2.79 | 0.57 | 5.92 | 10.39 | |

This representation of the objects (Table 3) can be applied as an input in commonly available systems for representing and analyzing the object size distribution and the shape properties thereof.

The new method can be used to give a better estimate of object properties than prior art where only one image of each object was used (or multiple images of the same object that was not identified as the same object.) The multiple images of each object can then be used to estimate different size and shape properties for each individual object. Like maximum length, minimum width, average volume and more complex size and shape properties.

This new invention will have large benefits in dynamic object imaging technology. One example of a better estimate is measurement of maximum length. If one measures the maximum length of each instance of an individual object, then the maximum value of these lengths gives a better estimate compared to the real maximum object length than the maximum length of a random instance of a particular object.

More complex properties can be the length/thickness ratio where the length is characterized by the maximum length of an individual object and the thickness by the minimum width of the same object, but not necessarily the same instance of this object.

Based on the improved estimates for each individual object, a more accurate result for the total sample can be created.

It should be understood that instead of generating a rotation of the objects, the imaging means can be arranged for performing a rotation about the objects. The objects can be stationary and resting on a transparent layer or the like, or they can move in the gravitational field or on a conveyor or the like while the imaging means performs orbital or helical motion relative to said objects.

The examples as described above relate to particles, but it should be understood that the principles of the present invention can be applied for any type of objects. For instance when classifying food products such as potatoes or the similar, or even fish.

The invention claimed is:

1. A method for analyzing objects contained in a flow or product sample to enable the calculation and monitoring of data including individual object size and shape, and common data including size distribution, the method comprising:
   providing at least one image capturing means for capturing images of said objects and means for generating relative mutual movement between said image capturing means and said objects;
   causing translatory and rotational movement of said objects; and
   capturing two or more images of said objects at different points in both time and space and at different angular positions of said objects, thus being able to image different projection areas of said objects, where the images are applied for further processing and analysis of said objects in a computer based image analyzer.

2. A method in accordance with claim 1, wherein each individual object of said objects is allowed to move in a plane substantially perpendicular to a view axis of said image capturing means, where a first image ($b_1$) of the object is captured at a time $t_1$ and a next image ($b_2$) is captured at a time $t_2=t_1+\Delta\tau$.

3. A method in accordance with claim 2, wherein a center point of the object captured at time ($t_1$) is defined on the basis of the first image $b_1$ and then an estimate of the position of a center point of the object captured at time ($t_2$) in image $b_2$ is calculated, and further a tolerance area with a center thereof in the object captured at time ($t_2$) is calculated, then if one object in image $b_2$ has its center within said tolerance area, a match is found.

4. A method in accordance with claim 3, wherein the object is accepted as being another representation of the corresponding object in the first image ($b_1$) if an area thereof is within a certain size tolerance.

5. A method in accordance with claim 4, wherein if no objects are found that are within the certain size tolerance, it will be assigned the next available ordinal object number in the sequence, unless the position of the object in ($b_2$) is larger than $$p_{x2}(0) + \frac{D_A}{2}$$

then the object is discarded,
   where $p_{x2}$ represents most likely pixel position and $D_A$ represents object diameter based on object area.

6. An apparatus for analyzing objects contained in a flow or product sample where data including individual object size and shape, and common data including size distribution can be calculated and monitored, the apparatus comprising:
   at least one image capturing means for capturing images of said objects thus representing a measuring volume;
   means for generating a relative mutual movement between said at least one image capturing means and said objects; and
   image processing and analyzing means for processing and analyzing images captured in the measuring volume represented by the image capturing means, wherein the relative mutual movement comprises translatory and rotational movement of said objects, thus establishing two or more images of the projected area of said objects at different points in both time and space and different angular positions relative to the image capturing means for further processing and analysis in said image processing and analyzing means.

7. An apparatus in accordance with claim 6, wherein the image processing and analyzing means comprises an image processing unit that identifies at least one of the objects in one image relative to the at least one object in a previous image.

8. An apparatus in accordance with claim 7, wherein the image processing unit comprises a computer based algorithm to recognize and verify the objects.

9. An apparatus in accordance with claim 8, wherein the objects are allowed to fall in a gravity field, and the objects to be analyzed are caused to rotate by a mechanical device.

10. An apparatus in accordance with claim 7, wherein the image capturing means is a mega pixel camera.

11. An apparatus in accordance with claim 10, wherein the objects are allowed to fall in a gravity field, and the objects to be analyzed are caused to rotate by a mechanical device.

12. An apparatus in accordance with claim 7, wherein the objects are allowed to fall in a gravity field, and the objects to be analyzed are caused to rotate by a mechanical device.

13. An apparatus in accordance with claim 6, wherein the objects are allowed to fall in a gravity field, and the objects to be analyzed are caused to rotate by a mechanical device.

14. An apparatus in accordance with claim 6, wherein said image processing and analyzing means comprises a computer based image analyzer.

* * * * *